(12) United States Patent
Rost

(10) Patent No.: US 6,383,143 B1
(45) Date of Patent: May 7, 2002

(54) RESPIRATORY MONITOR

(76) Inventor: Gerald A. Rost, 4650-143 Dublin Rd., Fallbrook, CA (US) 92028

(*) Notice: Subject to any disclaimer, the term of this patent is extended or adjusted under 35 U.S.C. 154(b) by 0 days.

(21) Appl. No.: 09/672,871

(22) Filed: Sep. 29, 2000

Related U.S. Application Data

(60) Provisional application No. 60/159,249, filed on Oct. 13, 1999.

(51) Int. Cl.$^7$ .................................................. A61B 5/08
(52) U.S. Cl. ........................................ 600/534; 600/529
(58) Field of Search .................................. 600/529, 534

(56) References Cited

U.S. PATENT DOCUMENTS

| | | |
|---|---|---|
| 3,782,368 A | 1/1974 | Reibold |
| 4,185,621 A | 1/1980 | Morrow |
| 4,443,730 A | 4/1984 | Kitamura et al. ............ 310/330 |
| 4,576,179 A | 3/1986 | Manus et al. |
| RE32,180 E | 6/1986 | Lewiner et al. ............. 340/573 |
| 4,909,260 A | 3/1990 | Salem et al. |
| 4,960,118 A * | 10/1990 | Pennock ................ 128/200.24 |
| 5,002,060 A | 3/1991 | Nedivi |
| 5,076,281 A * | 12/1991 | Gavish ........................ 128/721 |
| 5,161,541 A | 11/1992 | Bowman et al. |
| 5,448,996 A * | 9/1995 | Bellin et al. ................. 128/671 |
| 6,021,351 A | 2/2000 | Kadhiresan et al. .......... 607/19 |
| 6,024,088 A | 2/2000 | Ishikawa et al. |
| 6,064,910 A | 5/2000 | Anderson et al. ............. 607/20 |

FOREIGN PATENT DOCUMENTS

GB 2181555 * 4/1987 ............ A61B/5/08

* cited by examiner

*Primary Examiner*—Kevin Shaver
*Assistant Examiner*—Patricia Mallari
(74) *Attorney, Agent, or Firm*—Christopher Whewell

(57) ABSTRACT

This invention relates to respiratory sensors having a more favorable construction and method of attachment to the human body than analogous devices found in the prior art. Through use of the present invention, the gathering of accurate data over the passage of a greater time span than was previously possible may be readily achieved. Such higher quality data may be used by medical and other professionals to more accurately assess, study, and diagnose particular medical conditions, as well as body function and response to applied stress.

18 Claims, 4 Drawing Sheets

RESPIRATORY MONITOR

CROSS-REFERENCES TO RELATED APPLICATIONS

This application claims priority to U.S. Provisional Patent Application No. 60/159,249 which was filed on Oct. 13, 1999 and is currently still pending. The entire contents of said Provisional Patent application are herein incorporated by reference thereto.

TECHNICAL FIELD

This invention relates generally to devices useful in measuring and monitoring functional parameters of the human body. More particularly, the invention relates to sensors useful in the monitoring of respiration The sensors of the invention may be used in monitoring respiration under stress-free situations, such as during sleep, and may also be used under conditions of stress, such as during a lie detector test.

BACKGROUND

Various transducers useful in measuring respiration of the human organism may be found in the prior art. The following U.S. Patents, each of which are herein expressly incorporated by reference, are exemplary thereof.

U.S. Pat. No. 3,782,368 describes a transducer assembly comprising a piezoelectric element, an elastic belt, a fastening means, and specialized signal conditioning circuitry of various functions.

U.S. Pat. No. 4,185,621 describes a body worn parameter display devices which includes a housing having a display array, a piezoelectric sensing means for sensing a variable body pressure and delivering a representative electrical signal, a means for connecting the electrical output to the display array, and a means for supplying the piezoelectric means with electricity. The device is worn like a wristwatch and thus the piezoelectric elements are thus attached to the patient using a belt means.

U.S. Pat. No. 4,443,730 describes a multi-layer transducer device for attachment to the body. The device is attached by means of a cuff, which is the functional equivalent of a belt.

U.S. Pat. No. 4,576,179 describes a respiration monitoring device having a piezoelectric transducer mounted in a bridge-like arrangement on a pair of spaced piers that are connected by a flexible beam member. The sensing element of the device is attached to the patient by means of a belt.

U.S. Pat. No. 4,909,260 sets forth a belt adapted to fit on a body so as to undergo tension changes due to body expansion and contraction during breathing wherein the belt has a first sensing means with a preferential sensing axis for producing a breathing signal in response to opposing forces along the sensing axis and a holder means interposed in the belt as part thereof that operatively holds the sensing means with its sensing axis aligned generally transverse to tension in the belt, and for transforming a tension change in the belt at the sensing means to opposing forces directed along the transverse sensing axis to produce a breathing signal.

U.S. Pat. No. 4,960,118 sets forth a method for measuring respiration which includes measuring the rate of change of abdomen circumference using a piezoelectric sensor that provides an electrical output, with the piezoelectric sensor being attached to an extensible abdominal belt by means of a rivet, in which the piezoelectric sensor has an electrically-conductive coating on each of its sides. The rate of change of rib cage circumference is also measured using another piezoelectric sensor, with the piezoelectric sensor being attached to an extensible abdominal belt by means of a rivet, in which the piezoelectric sensor has an electrically-conductive coating on each of its sides. The outputs of the rib cage and abdominal sensors are weighted and summed so that the summed output represents total respiratory flow.

U.S. Pat. No. 5,002,060 sets forth a monitoring system adapted to simultaneously monitor cardiac and respiratory rates and characteristics and substantial changes in temperature of a living body. The system uses sensors which are passive and non-invasive, and remotely completely located off the living body such as piezoelectric sensors. The sensor means is adapted to detect respiration and heart beat signals, and is passive and remotely located off the body of the individual.

U.S. Pat. No. 5,161,541 sets forth an apparatus for monitoring respiration of a patient that includes a flexible substrate having three thermoresistive devices comprising a layer of conductive ink of high temperature coefficient of resistivity coupled in series and affixed to a substrate. There is a means for adhesively attaching the substrate to the patient using a strip of medical adhesive tape. No mention is made of a piezoelectric sensor, and no filtering circuitry is present on the sensing means.

U.S. Pat. No. 6,021,351 sets forth 1. Apparatus for assessing the well-being of a patient in whom a cardiac pacemaker is implanted to assess the efficacy of a given pacing therapy, comprising a sensor means for detecting a physiologic parameter of a patient on or in whom the sensor means is affixed and for producing electrical signals that vary with the patient's level of exertion. The sensor means may be a piezoelectric sensor. There is no specific mention of the means by which the sensor is attached to the patient, nor of the presence of any filtering circuitry in the transducer itself.

U.S. Pat. No. 6,024,088 teaches a breath-synchronization control unit for a gas feeder for supplying a gas from a source to a human in synchronization with breathing. The unit includes a breath-detecting sensor, wherein the breath detecting sensor includes a plate shaped piezoelectric element, a container having a single space to house said piezoelectric element, and a control section which opens and closes a valve of a gas source to supply gas for a predetermined time when said piezoelectric element of the breath-detecting sensor detects an inhalation attempt by sensing air pressure from the air vent hole.

U.S. Pat. No. 6,064,910 discloses a respiration detector that includes a sensor which generates an electrical signal containing a signal component produced by heart sounds, wherein the signal component has a varying amplitude. There is also an analyzer means for extracting the signal component and for analyzing variations of the amplitude of the signal component for identifying at least one of a respiration rate, and a respiration depth from the variations of the amplitude. No adhesive tape is disclosed and no filtering circuitry is disclosed as being a part of the transducing means.

Reissue U.S. Pat. No. 32,180 sets forth a flexible composite sheet which comprises layers which function as electromechanical transducers for a patient who lies upon them. No filtering circuitry is disclosed as being part of the construction and no mention is made of adhering the transducer to the body of a patient.

However, the teachings of the prior art suffers from the use of straps or belts to cause the prior art sensors to contact the subject person's body. The use of straps is undesirable because over even relatively short periods of time, normal movements of a patient's body cause the sensors which are held in place by such straps to become loosed from the straps and hence unable to collect the desired data. This situation is especially troublesome for those engaged in the study of sleep disorders, as such sensors routinely slide to incorrect body positions or fall off the patient during the evening.

Further, of the sensing means found in the prior art, none has thus far provided filtering circuitry which is part of an integral construction with the sensor itself Rather, the prior art has relied exclusively on remotely located filtering circuitry. Such separation of the location of the filtering circuitry and the sensor has lead to an increased electronic noise level, owing to the length of the wire between these elements.

Thus, if a respiratory sensor having a filtering circuit as an integral part of its construct were devised, such a device would provide a data acquisition device with more accuracy than its prior art counterpart. In addition, if such a sensor were also attachable to a human subject in such fashion as to be relatively un-noticeable, then the human subject would sense less anxiety associated with the wearing of such a sensor. Finally, if such means for attaching a sensor by such relatively un-noticeable fashion enabled the sensor to remain on a patient during their entire course of sleep during a study requiring monitoring of the person in the sleep state, such a device would enable uninterrupted data gathering and less re-testing than is associated with analogous sensors in the prior art. It is believed that if such a device displayed all of these characteristics there would be provided added benefit as well, owing to the combined effects of uninterrupted gathering of data, more comfortable mounting, and a decreased noise level, which are believed to complement one another to provide a synergy not available prior to the discovery of the present invention. The present invention provides such devices.

SUMMARY OF THE INVENTION

The present invention provides a substantially planar device useful for measuring respiration of a human subject and which may be directly attached to a human subject. A device according to the invention comprises in a single construction both a transducer that is capable of generating a voltage signal output in response to the motion of the torso during human respiration, and a filtering circuit connected to the output of the transducer, so as to reduce electrical noise levels. Such an arrangement enables a device according to the invention to be affixed to a patient not only by belts used conventionally for this purpose, but importantly enables such single construction to be affixed to a human subject by means of adhesive tape. Such a capability provides for the secure fitment of the device as a whole to the subject, in such fashion as to minimize discomfort and to ensure that the transducer does not become dislodged from its initial placement.

The invention also provides novel means using a plurality of adhesive tapes by which such a device is affixed to a subject, although a single piece of adhesive tape may be used, if desired.

DETAILED DESCRIPTION

Figure 1:
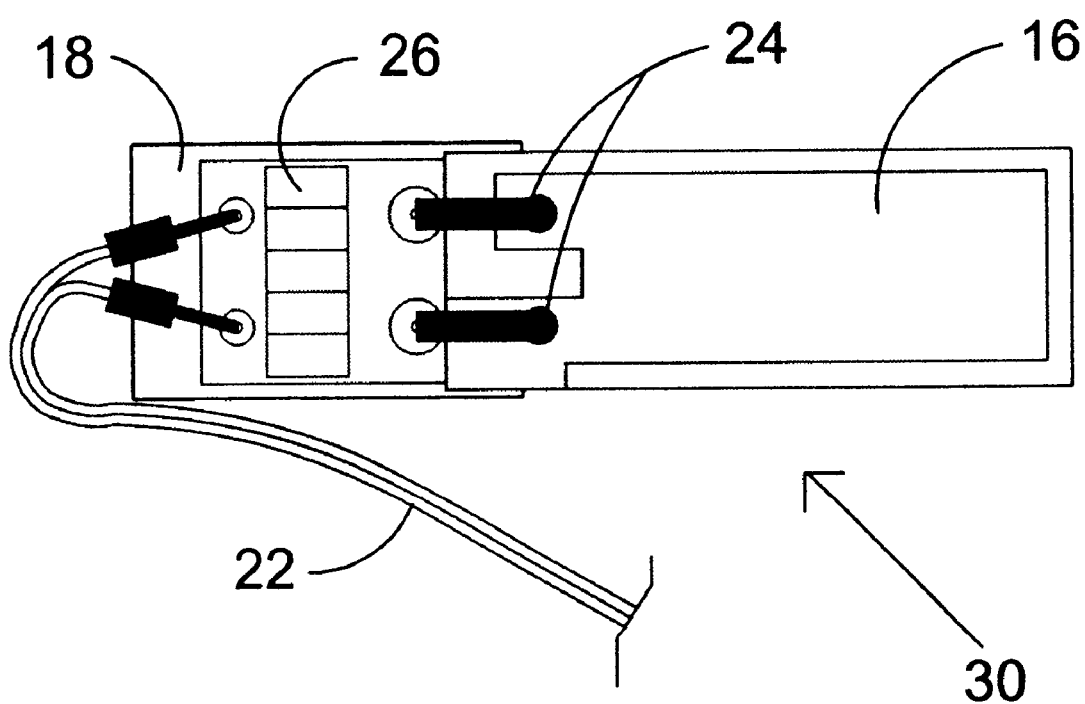
FIG. 1 is an overhead view of a device according to the invention.

Referring to the drawings and initially to FIG. 1 there is shown an overhead view of a combination 30 according to the invention in which 18 represents the filtering circuit portion and 16 represents a transducer, which in a preferred form of the invention is a piezoelectric transducer. The transducer has output signal leads 24 which are in effective electrical contact with the input leads on the filtering circuitry 26. There are device output leads 22 from which the output of the device as a whole is accessible, and which device output leads are connected to an amplifier or signal processor (not shown), as such means for processing signals generated by piezoelectric devices are well known in the art. One such signal processing means useful in connection with piezoelectric respiratory sensing devices according to the invention is the Polysomnograph model PSGRS 1, manufactured by the Grass Instrument Division of Astro-Med, Inc. of 600 East Greenwich Avenue, West Warwick, R.I. 02983. The use of these devices entails merely connecting the output leads from the sensing device to the input terminals on the signal processor, and making routine adjustments which are well known to those skilled in the art. Any such signal processing means which are recognized by those skilled as being useful with a filtered input of the magnitude that a piezoelectric sensor is capable of outputting may be used in processing the signals outputted by a device according to this invention. According to one form of the invention, the overall length of a device according to the invention is any length between about 1.5 inches long and about 12 inches long, with 3.0 inches being most preferred. According to one form of the invention, the overall width of a device according to the invention is any width between 0.7 inches wide and 2.0 inches wide, with 1.1 inches being most preferred. Thus, any combination of dimensions of the individual components of transducer and filtering circuitry which falls within these parameters is useful within the scope of this invention. According to one preferred form of the invention, the overall thickness of a device as herein provided is less than about 0.25 inches thick, more preferably less than 0.20 inches thick, and most preferably is 0.15 inches thick, but may be any thickness between about 0.1 and 0.3 inches thick.

Thus, a respiratory sensor provided in accordance with the invention comprises two distinct elements: 1) the transducer element 16; and 2) the filtering circuitry 18. Preferably, these elements are housed in a protective pouch to provide a sensor assembly 77, as shown later in exploded view in FIG. 3.

THE TRANSDUCER ELEMENT

Although this invention is especially well suited for the use of piezoelectric films as the transducer element, the present invention contemplates the use of other transducers known in the art which are capable of sensing motion and providing a voltage signal in response thereto. Such other transducers include without limitation ultrasonic transducers, magnetic transducers, and optical transducers, with the proviso that such transducers may be coupled with filtering circuitry in such fashion as to arrive at a finished construct which is capable of being attached to the body of a human subject under study in the same fashion that a sensor assembly including a piezoelectric film is attached to the body of a subject according to the teachings herein using adhesive tape.

The Piezoelectric effect has been known to those skilled in the art of solid state chemistry and physics for quite some time, and in a broad sense involves the generation of an electrical current in a solid in response to a stress applied to the solid. With the advent of modern film producing technologies (cast films and blown films) and the availability of a wide range of polymerized materials which may be formed into films, there have been discovered many piezoelectric film constructs, most or all of which are useful as an element of this invention.

A polymeric piezoelectric material having high piezoelectric performance, is disclosed in U.S. Pat. No. 3,931,446 which is a polyvinylidene fluoride based piezo transducer. Also reported are vinylidene fluoride copolymers in U.S. Pat. No. 4,204,135, Japanese Pat. (Kohkai) Nos. 56-111281 and 58-60585. Moreover, these vinylidene fluoride resins are reported to have high piezoelectric performance even in a high frequency region, as disclosed in U.S. Pat. No. 3,798,473. (The entire contents of these patents and publications are herein incorporated by reference thereto). These polymeric piezoelectric materials are generally formed into piezoelectric films by forming them into films according to rolling or casting, then applying heat treatment on the film surface in order to enhance the electromechanical coupling factor $K_t$ in the direction perpendicular thereto and applying an electric field in the direction perpendicular to the film to effect poling treatment. Among a series of these vinylidene fluoride resins, polyvinylidene fluoride has a $K_t$ value of about 0.2 and is also excellent in formability, thus being well adapted for use in ultrasonic transducers.

In practice, the transducer element of a sensing device according to the invention which is attached to a patient under observation is stressed by the normal expansion and contraction of the chest wall or abdominal wall, depending upon sensor placement. Such stress produces a voltage signal from the transducer, which is immediately passed through the electronic filtering circuitry before the respiratory effort signal is applied onto a physiological monitoring or recording system.

The types of piezoelectric films which are most suitable for use in the present invention are Plastic polymers. Such films are exemplified by polyvinylidene fluoride, a film made by the Pennwalt Corporation, Valley Forge, Pa. 19482 under the trade name of KYNAR®. Such films are especially preferred because of its large dipole moment, wide frequency band characteristics, low Q and excellent impedance match to human tissue. This film is processed into piezoelectric sensors by Measurement Specialties, Inc., 950 Forge Avenue, Norristown, Pa. 19403.

Any film which has similar piezoelectric characteristics and which puts out a voltage between 200 microvolts and 2000 microvolts in response to a mechanically centered deflection of about 1/16 (0.062) inches after attenuation by the passive filter is suited for use in the present invention.

THE FILTERING CIRCUITRY

Figure 2:
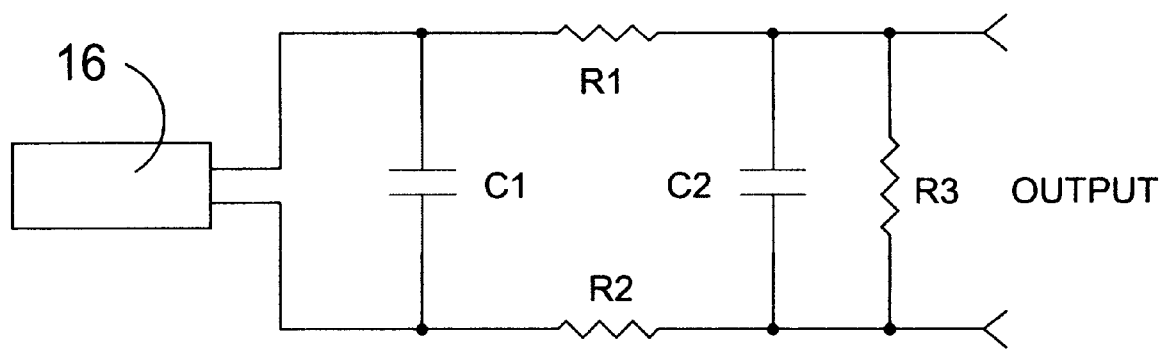
FIG. 2 is a schematic diagram of a filtering circuit useful as an element of a device according to the invention.

Another element of the present invention is the filtering circuitry, which has the purpose of eliminating frequencies greater than 15 Hertz (Hz) from a transducer (such as a piezoelectric sensor) so that the subsequent bioamplifier will amplify only low frequency signals, such as, in particular, those caused by respiration. Since such is a relatively simple function, the means by this result may be achieved by any one of a number of filtering circuitries known to those skilled in the art of electronic signal processing. However, it is most preferable to use the circuit shown in FIG. 2 in conjunction with the other elements of the invention. In this circuit, 16 represents the transducer, which is preferably a piezoelectric film as just described. The preferred values for the components are: R1=4.3M$\Omega$; R2=4.3M$\Omega$; R3=500K$\Omega$; C1=0.33$\mu$Fd; and C1=0.33$\mu$Fd. Such values are selected to provide a low pass passive filter which eliminates frequencies above 15 Hz, which may thus be conveniently thought of as being a "cutoff frequency". This type of filtering circuitry is useful with the piezoelectric film transducer mentioned and works especially well in measuring respiration. However, the cutoff frequency of 15 Hz mentioned above may be tailored to any value, using appropriate substitution of electrical components in the filtering circuit as such substitutions are known to those of ordinary skill in the electronic arts. Thus, cutoff values (in Hz) of 14, 13, 12, 11, 10, 9, 8, 7, 6, 5, 4, 3, 2, and 1 Hz are all useful in accordance with the invention.

A respiratory sensing device according to the invention may be attached to a patient to be monitored using the conventional belts disclosed in the prior art references cited earlier. However, according to one preferred form of the invention, equivalent signals may be achieved compared with using the belts of the prior art, by using two disposable adhesive strips to hold the re-usable sensor onto the patient instead of the conventional strap retention means. Such second side is then contacted on the patient in the desired location, typically the chest or the abdomen. After ascertaining that an adequate respiratory effort signal is present, the sensor is then overlaid with a larger piece of highly flexible tape having an adhesive on one side, to secure the sensor to the patient. Both tapes are specifically designed for adhesion to skin surfaces for extended periods of time, and such tapes are well known to those skilled in the art.

Figure 3:
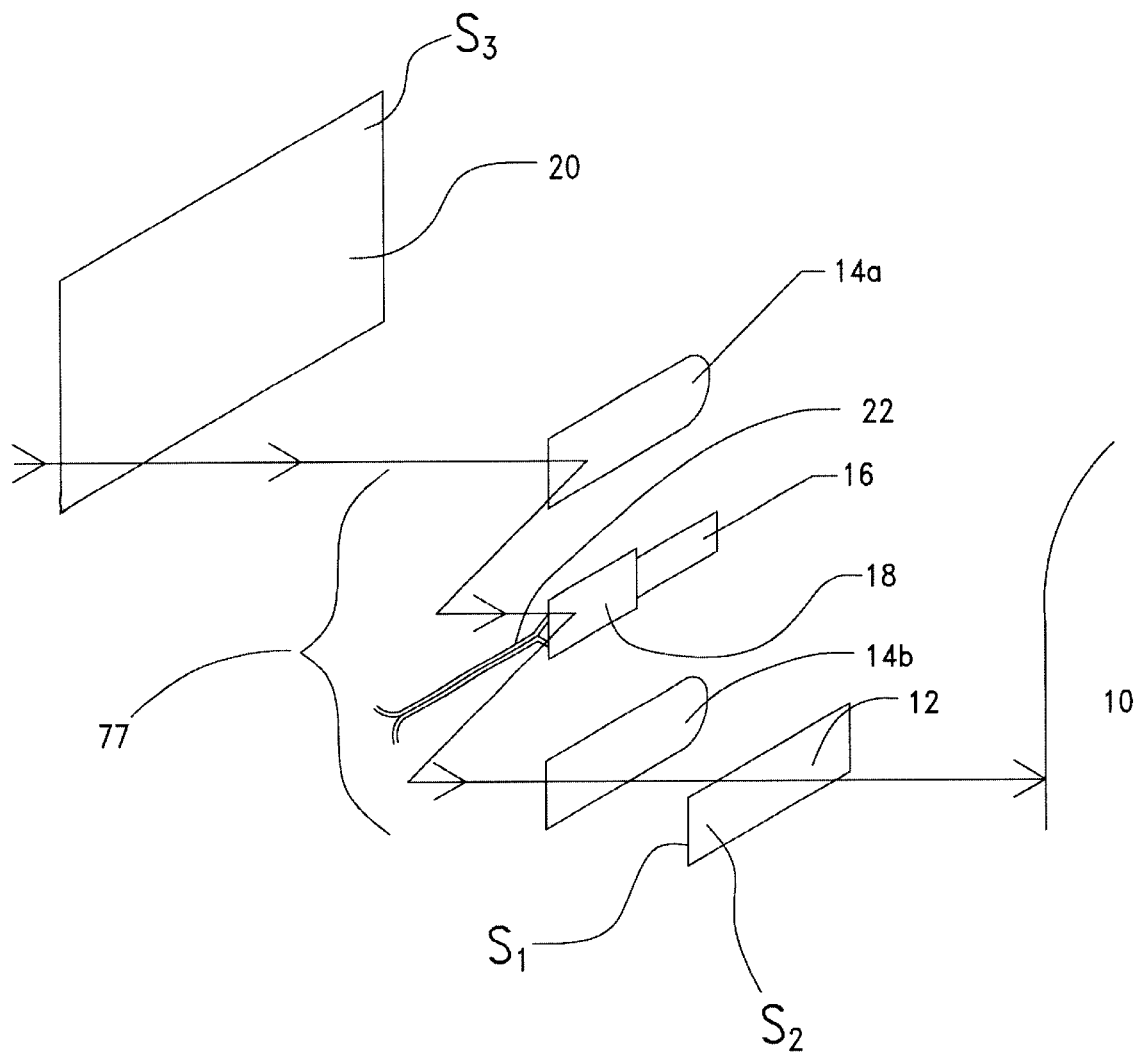
FIG. 3 is an exploded view of a device according to the invention and sundry components useful in conjunction therewith.

The order of the elements used in affixation of a sensor according to such a preferred form of the invention is outlined in FIG. 3, in which is shown the sensor assembly 77, that comprises the transducer/filtering circuitry combination 30, a front pouch panel portion 14a, and a rear pouch panel portion 14b. The front pouch panel portion 14a and the rear pouch panel portion 14b are conveniently sewn to one another about at least three sides of their perimeter to provide a pouch into which the combination 30 may be inserted. Thus, the sensor assembly 77 preferably comprises the combination 30 disposed within a thin pouch. Preferably, the front pouch panel portion 14a and the rear pouch panel portion 14b are constructed of a thin cloth or plastic material, preferably a water-repellant material, as such water-repellant materials are well-known in the art. However, any cloth is useful in this regard, with the main proviso being that the cloth must not materially interfere with the collection of data from the subject.

For use of a combination according to a preferred form of the invention, a sensor assembly 77 is contacted with the adhesive on surface $S_1$ of a strip of double sided adhesive tape 12, which adhesive tape has a length dimension at least as long as the assembly 77. Next, the release sheet on the other side $S_2$ of the double-sided adhesive strip is removed, and it is this side which is affixed to the patient 10 under study. Once it has been ascertained that the sensing device is properly placed on the subject, then a large adhesive patch 20 having adhesive on only one side ($S_3$) is placed over all of the aforesaid components, to provide an arrangement as shown in FIG. 4.

Figure 4:
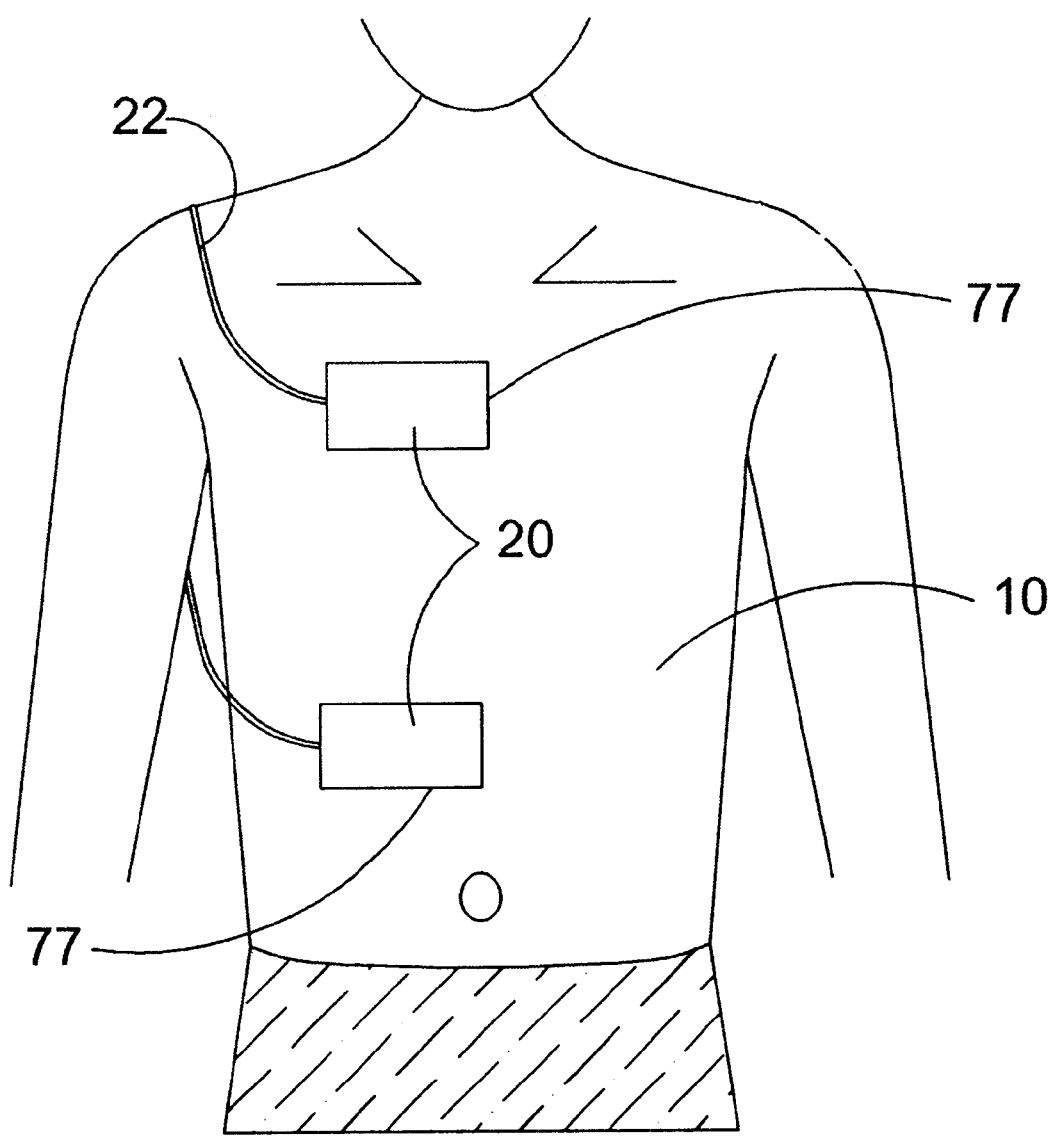
FIG. 4 is a frontal view of a human subject to whom sensing means according to the invention is affixed.

FIG. 4 depicts a subject 10 to whom a plurality of the sensing means according to the invention have been affixed. Here are visible the large adhesive patches 20 which have been placed over the remaining components shown in exploded view in FIG. 3 for each of the abdominal sensor and a thorax sensor used. Also shown are the device output leads 22.

For purposes of this invention and the appended claims the words "substantially planar" when used in describing a device according to the invention means that such device is planar enough or flat enough in its construction so as to be placed on a portion of the torso of a human subject and subsequently affixed to such human subject by means of an ordinary two-sided adhesive tape being applied over the device so as to cover at least 20% of the surface area of such device which is in contact with the human subject. According to a preferred form of the invention, a device provided in accordance with the invention is capable of being placed onto the torso of a human subject and subsequently affixed to such human subject by means of two sided adhesive tape being applied over the device to cover any amount between about 20% and 100% of the surface area of such device which is in contact with the human subject. It is most preferred that a device according to the invention is capable of being placed on a portion of the torso of a human subject and subsequently affixed to such human subject by means of an ordinary adhesive tape being applied over the device so as to completely cover the device.

Thus, a device according to the invention need not necessarily be absolutely flat, but may have some degree of relief, provided the above criteria are met. However, given the small size of the circuitry that may be used as an element of the invention as a whole in a preferred embodiment, and given the planar nature of the piezoelectric films that may be used as an element of the invention as a whole in a preferred embodiment, it has been found that providing very flat completely constructed devices according to the invention having any thickness in the range of between about 0.04 inches and about 0.20 inches is readily achievable.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

I claim:

1. A process for attaching a transducer to the body which comprises the steps of:
    a) providing a transducer having an upper face and a lower face;
    b) providing a first adhesive tape having a first face and a second face, and having an adhesive substance disposed on each of said faces;
    c) contacting the adhesive on said first face of said adhesive tape to said upper face on said transducer;
    d) contacting the adhesive on said second face of said adhesive tape to a human subject so as to cause said transducer to be affixed to said subject.

2. A process according to claim 1 further comprising:
    e) providing a second adhesive tape having a greater surface area than said first adhesive tape, and having a first face and a second face, and having an adhesive substance disposed on one of said first face or second face of said second adhesive tape;
    f) placing said second adhesive tape over said transducer so that said adhesive substance disposed on said second adhesive tape contacts said subject.

3. In the use of a piezoelectric sensor useful for measuring respiration of a human subject, wherein the improvement comprises: providing a single device comprising a piezoelectric film in cooperative electrical and physical contact with a filtering circuit, wherein such article may be affixed to said human subject with adhesive tape.

4. A substantially planar device useful for measuring respiration of a human subject and which may be directly attached to a human subject, comprising in a single construction:
    a) a transducer capable of generating a voltage signal output in response to the motion of the torso during human respiration, wherein said transducer comprises output signal leads;
    b) a filtering circuit, having means for receiving an input signal, and comprising output signal leads,
wherein said output signal leads of said transducer are connected to said means for receiving an input signal of said filtering circuit, wherein said transducer is a piezoelectric film, and wherein said filtering circuit is mounted directly to said piezoelectric film.

5. A device according to claim 4 wherein said piezoelectric film comprises at least one polymer selected from the group consisting of: polyvinylchloride, polyethylene, polypropylene, poiyvinylidene fluoride, polyvinylidene chloride, ethylene vinyl acetate, polyphenylene oxide, polysulfone, polyphenylsulfone, polyether sulfone, polyphenylene sulfide, polyetherimide, polyetheretherketone, polyacetals, or polyethylene terephthalate.

6. A device according to claim 4 wherein said piezoelectric film generates a voltage of at least 50,000 microvolts, peak to peak, in response to a human breathing cycle.

7. A device according to claim 6 wherein said filtering circuit reduces the signal voltage to a value less than 500 microvolts, peak to peak, in response to said breathing cycle.

8. A device according to claim 6 wherein said filtering circuit reduces the signal voltage to a value of about 150 microvolts, peak to peak, in response to said breathing cycle.

9. A process for measuring human respiration comprising the steps of:
    a) providing a device according to claim 6, wherein said device has an upper face and a lower face; and
    b) attaching said device to a human subject by steps comprising:
        i) providing a first adhesive tape having a first face and a second face, and having an adhesive substance disposed on each of said faces;
        ii) contacting the adhesive on said first face of said adhesive tape to said upper face on said transducer;
        iii) contacting the adhesive on said second face of said adhesive tape to a human subject so as to cause said transducer to be affixed to said subject; and
    c) monitoring the variations in the voltage output of said device.

10. A device according to claim 4 wherein the signal leads of the transducer which are connected to the means for receiving an input signal of the filtering circuit are no greater than ten feet long.

11. A device according to claim 4 wherein the signal leads of the transducer which are connected to the means for receiving an input signal of the filtering circuit are no greater than one inch long.

12. A device according to claim 4 further comprising:

c) a signal processor having input leads, wherein said output signal leads of said filtering circuit are connected to the input leads of said signal processor.

13. A device according to claim 4 wherein said filtering circuit attenuates all signals above 15 Hz.

14. A process for measuring human respiration comprising the steps of:

a) providing a device according to claim 4; and
b) monitoring the variations in the voltage output of said device.

15. A process for measuring human respiration comprising the steps of:

a) providing a device according to claim 4, wherein said device has an upper face and a lower face; and
b) attaching said device to a human subject by steps comprising:
  i) providing a first adhesive tape having a first face and a second face, and having an adhesive substance disposed on each of said faces;
  ii) contacting the adhesive on said first face of said adhesive tape to said upper face on said transducer;
  iii) contacting the adhesive on said second face of said adhesive tape to a human subject so as to cause said transducer to be affixed to said subject; and;
c) monitoring the variations in the voltage output of said device.

16. A process according to claim 15 wherein said attaching step further comprises the steps of:

iv) providing a second adhesive tape having a greater surface area than said first adhesive tape, and having a first face and a second face, and having an adhesive substance disposed on one of said first face or second face of said second adhesive tape; and
v) placing said second adhesive tape over said transducer so that said adhesive substance disposed on said second adhesive tape contacts said subject.

17. A substantially planar device useful for measuring respiration of a human subject which comprises:

a) a transducer capable of generating a voltage signal output in response to the motion of the torso during human respiration, wherein said transducer has a bottom surface and a top surface, and wherein said transducer comprises output signal leads;
b) filtering circuit, having means for receiving an input signal, and comprising output signal leads, wherein said output signal leads of said transducer are connected to said means for receiving an input signal of said filtering circuit;
c) at least one strip of adhesive tape having a first surface and a second surface, wherein said adhesive tape comprises adhesive on both of said surfaces, wherein said first surface of said tape is in contact with said top surface of said transducer.

18. A device according to claim 17 further comprising:

d) a signal processor having input leads, wherein said output signal leads of said filtering circuit are connected to the input leads of said signal processor.

\* \* \* \* \*